(12) United States Patent
Ackermann et al.

(10) Patent No.: US 8,552,024 B2
(45) Date of Patent: *Oct. 8, 2013

(54) AZACYCLIC COMPOUNDS

(75) Inventors: Jean Ackermann, Riehen (CH); Aurelia Conte, Basel (CH); Daniel Hunziker, Moehlin (CH)

(73) Assignee: Hoffman-La Roche Inc., Nutley, NJ (US)

( * ) Notice: Subject to any disclaimer, the term of this patent is extended or adjusted under 35 U.S.C. 154(b) by 30 days.

This patent is subject to a terminal disclaimer.

(21) Appl. No.: 13/204,743

(22) Filed: Aug. 8, 2011

(65) Prior Publication Data

US 2012/0041013 A1    Feb. 16, 2012

(51) Int. Cl.
*C07D 471/10* (2006.01)
*A61K 31/438* (2006.01)

(52) U.S. Cl.
USPC .............................. 514/278; 546/16

(58) Field of Classification Search
USPC .......................... 546/16; 514/278
See application file for complete search history.

(56) References Cited

U.S. PATENT DOCUMENTS

2011/0112097 A1    5/2011    Jaehne et al.

FOREIGN PATENT DOCUMENTS

WO    2007/067504    6/2007
WO    2009/097997    8/2009

OTHER PUBLICATIONS

Hartwig, John, "Angewandte Chemie International Edition" 37(15):2046-2067 ( 1998).
International Search Report PCT/EP2011/063727 mailed Nov. 2, 2011.

*Primary Examiner* — Rita Desai

(57) ABSTRACT

The invention provides novel compounds having the general formula (I)

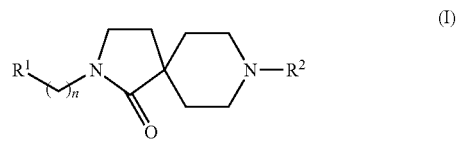

(I)

wherein $R^1$, $R^2$ and n are as described herein, compositions including the compounds and methods of using the compounds. The compounds are useful as inhibitors of hormone sensitive lipase (HSL) for the treatment of diabetes, metabolic syndrome and obesity.

3 Claims, No Drawings

AZACYCLIC COMPOUNDS

PRIORITY TO RELATED APPLICATION(S)

This application claims the benefit of European Patent Application No. 10172747.7, filed Aug. 13, 2010, which is hereby incorporated by reference in its entirety.

FIELD OF THE INVENTION

The present invention relates to organic compounds useful for therapy or prophylaxis in a mammal, and in particular to inhibitors of hormone sensitive lipase (HSL) for the treatment of diabetes, metabolic syndrome and obesity.

BACKGROUND OF THE INVENTION

The main physiological role of white adipose tissue (WAT) is to supply energy when it is needed by other tissues. In mammals, white adipose tissue is the primary energy storage depot, accumulating fuel reserves in the form of triacylglycerol (TAG) during times of energy excess. The release of free fatty acids (FFA) from TAG is stimulated by catecholamines and regulated by hormones such as insulin, glucagon and epinephrine. The most important enzyme in WAT believed responsible for hormone regulated hydrolysis of triglyceride is hormone sensitive lipase (HSL).

Dysregulation of adipocyte lipolysis, resulting in elevated circulating non-esterified fatty acids (NEFA) is associated with obesity and co-morbidities including the development of type 2 diabetes. Obese or insulin resistant subjects have increased visceral adipose tissue depots. These depots contain elevated levels of HSL protein and exhibit enhanced lipolytic activity as they are resistant to the insulin-mediated suppression of lipolysis. This results in increased plasma levels of free fatty acids (FFA), which further exacerbates insulin resistance due to the accumulation of triglycerides in tissues other than WAT such as liver, pancreas and muscle. Thus, the elevated plasma levels of FFA due to increased HSL activity contributes to and worsens insulin resistance in obese and type 2 diabetic individuals. Restoring the exaggerated plasma FFA and triglyceride levels through inhibition of HSL would reduce the accumulation of triglycerides in tissues other than WAT, such as liver, muscle and the pancreas resulting in decreased hepatic glucose output, increased muscle fatty acid oxidation and improving β-cell function.

Elevated FFAs are also associated with increased cardiovascular risk, including atherosclerosis and myocardial dysfunction. Furthermore high lipolytic activity and elevated FFAs lead to increased insulin resistance and hypertension in hypertensive rats. The FFA collect in the liver and lead to increased production of TAG, which are packaged into very low density lipoproteins (VLDL) which are secreted. Therefore, reducing the activity of HSL would decrease the release of FFA to the blood, thus limiting the supply of FFA to the liver for TAG synthesis. Thus, HSL inhibitors could have beneficial effects as treatment of nonalkoholic fatty liver disease (NAFLD) and nonalkoholic steatohepatitis (NASH).

SUMMARY OF THE INVENTION

The present invention relates to compounds according to formula (I)

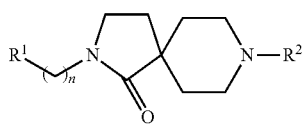

(I)

wherein:

$R^1$ is selected from the group consisting of: imidazolyl, pyrazolyl, triazolyl, phenyl, pyridinyl, pyrazinyl, pyrimidyl, pyridazinyl and 2-oxo-1,2-dihydro-pyridinyl, and is optionally substituted with one to three substituents independently selected from the group consisting of alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, haloalkyl, hydroxy, hydroxyalkyl, alkoxy, alkoxyalkyl, haloalkoxy, hydroxyalkoxy, alkoxyalkoxy, alkoxyalkoxyalkyl and hydroxyhaloalkyl;

$R^2$ is selected from the group consisting of: imidazolyl, pyrazolyl, triazolyl, phenyl, pyridinyl, pyrazinyl, pyrimidyl, pyridazinyl and 2-oxo-1,2-dihydro-pyridinyl, and is optionally substituted with one to three substituents independently selected from the group consisting of: alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, haloalkyl, hydroxy, hydroxyalkyl, alkoxy, alkoxyalkyl, haloalkoxy, hydroxyalkoxy, alkoxyalkoxy, alkoxyalkoxyalkyl, hydroxyhaloalkyl and benzyloxy; and n is zero, 1, 2 or 3.

The present invention also relates to pharmaceutically acceptable salts and esters of the aforementioned compounds.

Further objects of the present invention include the use of the compounds of formula (I) and their aforementioned salts and esters as therapeutically active substances, a process for the manufacture of said compounds, intermediates, pharmaceutical compositions and medicaments containing said compounds, or their pharmaceutically acceptable salts or esters, the use of said compounds, or salts or esters thereof, for the treatment or prophylaxis of illnesses, especially in the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis and the use of the said compounds, or salts or esters thereof, for the production of medicaments for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis.

DETAILED DESCRIPTION OF THE INVENTION

The present invention relates to compounds according to formula (I)

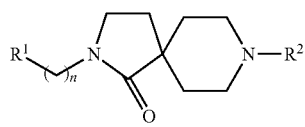

(I)

wherein:

$R^1$ is selected from the group consisting of: imidazolyl, pyrazolyl, triazolyl, phenyl, pyridinyl, pyrazinyl, pyrimidyl, pyridazinyl and 2-oxo-1,2-dihydro-pyridinyl, and is optionally substituted with one to three substituents independently selected from the group consisting of: alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, haloalkyl, hydroxy, hydroxyalkyl, alkoxy, alkoxyalkyl, haloalkoxy, hydroxyalkoxy, alkoxyalkoxy, alkoxyalkoxyalkyl and hydroxyhaloalkyl;

$R^2$ is selected from the group consisting of: imidazolyl, pyrazolyl, triazolyl, phenyl, pyridinyl, pyrazinyl, pyrimidyl, pyridazinyl and 2-oxo-1,2-dihydro-pyridinyl, and is optionally substituted with one to three substituents independently selected from the group consisting of: alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, haloalkyl, hydroxy, hydroxyalkyl, alkoxy, alkoxyalkyl, haloalkoxy, hydroxyalkoxy, alkoxyalkoxy, alkoxyalkoxyalkyl, hydroxyhaloalkyl and benzyloxy; and n is zero, 1, 2 or 3.

The present invention also relates to pharmaceutically acceptable salts and esters of the aforementioned compounds.

The term "alkyl", alone or in combination, signifies a straight-chain or branched-chain alkyl with 1 to 8 carbon atoms, in particular with 1 to 6 carbon atoms and further particular with 1 to 4 carbon atoms. Examples are methyl, ethyl, propyl, isopropyl, n-butyl, isobutyl, tert-butyl, n-pentyl, methylbutyl, dimethylpropyl, ethylpropyl, n-hexyl, methylpentyl, dimethylbutyl, trimethylpropyl and ethylmethylpropyl. Particular examples are methyl, ethyl, propyl, isopropyl, butyl, isobutyl and dimethylpropyl. Further particular examples are methyl and propyl.

The term "cycloalkyl", alone or in combination, signifies a cycloalkyl ring with 3 to 8 carbon atoms and in particular with 3 to 6 carbon atoms. Examples are cyclopropyl, cyclobutyl, cyclopentyl, cyclohexyl, cycloheptyl and cyclooctyl. A particular example is cyclopropyl.

The term "alkylcycloalkyl", alone or in combination, signifies a cycloalkyl, wherein one or more hydrogen atoms are replaced by an alkyl. Examples are methyl-cyclopropyl, dimethyl-cyclopropyl, methyl-cyclobutyl, dimethyl-cyclobutyl, methyl-cyclopentyl, dimethyl-cyclopentyl, methyl-cyclohexyl and dimethyl-cyclohexyl. Particular examples are methyl-cyclopropyl and dimethyl-cyclopropyl.

The term "cycloalkylalkyl", alone or in combination, signifies an alkyl, wherein one or more hydrogen atoms are replaced by a cycloalkyl. Examples are cyclopropylmethyl, cyclopropylethyl, cyclobutylmethyl, cyclobutylethyl, cyclopentylmethyl, cyclopentylethyl, cyclohexylmethyl, cyclohexylethyl, cycloheptylmethyl, cycloheptylethyl, cyclooctylmethyl and cyclooctylethyl. Particular examples are cyclopropylmethyl, cyclopropylethyl, cyclobutylmethyl and cyclobutylethyl.

The term "cycloalkylalkoxy", alone or in combination, signifies an alkoxy, wherein one or more hydrogen atoms are replaced by a cycloalkyl. Examples are cyclopropylmethoxy, cyclobutylmethoxy, cyclopentylmethoxy, cyclohexylmethoxy, cycloheptylmethoxy and cyclooctylmethoxy.

The term "cycloalkylalkoxyalkyl", alone or in combination, signifies an alkyl, wherein one or more hydrogen atoms are replaced by a cycloalkylalkoxy. Examples are cyclopropylmethoxymethyl, cyclopropylmethoxyethyl, cyclobutylmethoxymethyl, cyclobutylmethoxyethyl, cyclopentylmethoxyethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkoxy", alone or in combination, signifies a group of the formula cyloalkyl-O— in which the term cycloalkyl has the previously given significance. Examples are cyclopropoxy, cyclobutoxy, cyclopentyloxy, cyclohexyloxy, cycloheptyloxy and cyclooctyloxy.

The term "cycloalkoxyalkyl", alone or in combination, signifies an alkyl, wherein one or more hydrogen atoms are replaced by a cyclolalkoxy. Examples are cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "alkylcycloalkylalkyl", alone or in combination, signifies an alkyl, wherein one or more hydrogen atoms are replaced by an alkylcycloalkyl. Examples are methyl-cyclopropylmethyl, dimethyl-cyclopropylmethyl, methyl-cyclopropylethyl, dimethyl-cyclopropylethyl, methyl-cyclobutylmethyl, dimethyl-cyclobutylmethyl, methyl-cyclobutylethyl, dimethyl-cyclobutylethyl, methyl-cylopentylmethyl, dimethyl-cylopentylmethyl, methyl-cyclopentylethyl, dimethyl-cyclopentylethyl, methyl-cyclohexylmethyl, dimethyl-cyclohexylmethyl, methyl-cyclohexylethyl, dimethyl-cyclohexylethyl, methyl-cycloheptylmethyl, dimethyl-cycloheptylmethyl, methyl-cycloheptylethyl, dimethyl-cycloheptylethyl, methyl-cyclooctylmethyl, dimethyl-cyclooctylmethyl, methyl-cyclooctylethyl and dimethyl-cyclooctylethyl.

The term "halocycloalkyl", alone or in combination, signifies a cycloalkyl as defined before, wherein one or more hydrogen atoms are replaced by a halogen, in particular fluorine. Examples of halocycloalkyl are fluorocyclopropyl, difluorocyclopropyl, fluorocyclobutyl or difluorocyclobutyl.

The term "halocycloalkylalkyl", alone or in combination, signifies an alkyl as defined before, wherein one or more hydrogen atoms are replaced by a halocycloalkyl. Examples of halocycloalkyl are fluorocyclopropylmethyl, fluorocyclopropylethyl, difluorocyclopropylmethyl, difluorocyclopropylethyl, fluorocyclobutylmethyl, fluorocyclobutylethyl, difluorocyclobutylmethyl or difluorocyclobutylethyl.

The terms "halogen" and "halo", alone or in combination, signify fluorine, chlorine, bromine or iodine. Particular examples are fluorine or chlorine.

The term "haloalkyl", alone or in combination, signifies an alkyl as defined before, wherein one or more hydrogen atoms are replaced by a halogen, in particular fluorine. Examples of haloalkyl are fluoromethyl, difluoromethyl, trifluoromethyl, trifluoroethyl, trifluoromethylethyl or pentafluoroethyl. A particular example is trifluoromethyl.

The term "hydroxy", alone or in combination, signifies the —OH group.

The term "hydroxyalkyl", alone or in combination, signifies an alkyl as defined before, wherein one or more hydrogen atoms are replaced by a hydroxy. Examples of hydroxyalkyl are hydroxymethyl, hydroxyethyl, hydroxypropyl, hydroxymethylpropyl and dihydroxypropyl. Particular examples are hydroxyethyl and hydroxymethylpropyl.

The term "alkoxy", alone or in combination, signifies a group of the formula alkyl-O— in which the term alkyl has the previously given significance. Examples are methoxy, ethoxy, n-propoxy, isopropoxy, n-butoxy, isobutoxy, sec-butoxy and tert-butoxy. Particular examples are methoxy.

The term "alkoxyalkyl", alone or in combination, signifies an alkyl as defined before, wherein one or more hydrogen atoms are replaced by an alkoxy. Examples are methoxymethyl, ethoxymethyl, methoxymethyl, ethoxyethyl, methoxypropyl and ethoxypropyl.

The term "haloalkoxy", alone or in combination, signifies an alkoxy as defined before, wherein one or more hydrogen atoms are replaced by a halogen, in particular fluorine. Examples of haloalkoxy are fluoromethoxy, difluoromethoxy, trifluoromethoxy, trifluoroethoxy, trifluoromethylethoxy, trifluorodimethylethoxy, or pentafluoroethoxy. Particular examples are trifluoromethoxy and trifluoromethylethoxy.

The term "hydroxyalkoxy", alone or in combination, signifies an alkoxy as defined before, wherein one or more hydrogen atoms are replaced by a hydroxy. Examples of hydroxyalkoxy are hydroxyethoxy, hydroxypropoxy, hydroxymethylpropoxy and dihydroxypropoxy.

The term "alkoxyalkoxy", alone or in combination, signifies an alkoxy as defined before, wherein one or more hydrogen atoms are replaced by an alkoxy. Examples of methoxymethoxy, ethoxymethoxy, methoxymethoxy, ethoxyethoxy, methoxypropoxy and ethoxypropoxy.

The term "alkoxyalkoxyalkyl", alone or in combination, signifies an alkyl as defined before, wherein one or more hydrogen atoms are replaced by an alkoxyalkoxy. Examples of methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "hydroxyhaloalkyl", alone or in combination, signifies an alkyl as defined before, wherein one or more hydrogen atoms of the alkyl are replaced by a hydroxy and wherein one or more hydrogen atoms of the alkyl are replaced by a halogen, in which the terms hydroxy and halogen have the previously given significances. Examples of hydroxyhaloalkyl are hydroxytrifluoroethyl, hydroxytrifluoropropyl, hydroxyhexafluoropropyl.

The term "protecting group" refers to groups which are used to block the reactivity of functional groups such as amino groups or hydroxy groups. Examples of protecting groups are tert-butoxycarbonyl (Boc), benzyloxycarbonyl (Cbz), fluorenylmethoxycarbonyl (Fmoc) or benzyl (Bn). A particular protecting group is benzyl (Bn).

Cleavage of protecting groups can be done using standard methods known by the man skilled in the art such as hydrogenation or in the presence of an acid, e.g. HCl or TFA, or a base, e.g. triethylamine.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

A further embodiment of the present invention are compounds according to formula (I) as described above, wherein $R^1$ is selected from the group consisting of: phenyl, pyridinyl, pyrazinyl, pyrimidyl, pyridazinyl and 2-oxo-1,2-dihydro-pyridinyl, and is optionally substituted with one to three substituents independently selected from the group consisting of: alkyl, cycloalkyl, alkylcycloalkyl, cycloalkylalkyl, cycloalkylalkoxy, cycloalkylalkoxyalkyl, alkylcycloalkylalkyl, halocycloalkyl, halocycloalkylalkyl, halogen, haloalkyl, hydroxy, hydroxyalkyl, alkoxy, alkoxyalkyl, haloalkoxy, hydroxyalkoxy, alkoxyalkoxy, alkoxyalkoxyalkyl and hydroxyhaloalkyl.

A particular embodiment of the present invention are compounds according to formula (I) as described above, wherein $R^1$ is phenyl substituted with one to three haloalkoxy groups.

A particular embodiment of the present invention are compounds according to formula (I) as described above, wherein $R^1$ is trifluoromethoxyphenyl or 2,2,2-trifluoro-1-methylethoxyphenyl.

In a further embodiment of the present invention are compounds according to formula (I) as described above, wherein $R^2$ is selected from the group consisting of: phenyl, pyridinyl, pyrazinyl, pyrimidyl, pyridazinyl and 2-oxo-1,2-dihydro-pyridinyl, and is optionally substituted with one to three substituents independently selected from the group consisting of: alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, haloalkyl, hydroxy, hydroxyalkyl, alkoxy, alkoxyalkyl, haloalkoxy, hydroxyalkoxy, alkoxyalkoxy, alkoxyalkoxyalkyl, hydroxyhaloalkyl and benzyloxy.

The present invention also relates to compounds according to formula (I) as described above, wherein R² is selected from the group consisting of: phenyl, pyridinyl and 2-oxo-1,2-dihydro-pyridinyl,
and is optionally substituted with one to three substituents independently selected from alkyl, halogen, haloalkyl, hydroxy, alkoxy, haloalkoxy and benzyloxy.

An alternative embodiment of the present invention are compounds according to formula (I) as described above, wherein R² is pyridinyl or 2-oxo-1,2-dihydro-pyridinyl, and is optionally substituted with one to three substituents independently selected from alkyl and hydroxy.

A particular embodiment of the present invention are compounds according to formula (I) as described above, wherein R² is pyridinyl substituted with hydroxy or 2-oxo-1,2-dihydro-pyridinyl substituted with alkyl.

A further embodiment of the present invention are compounds according to formula (I) as described above, wherein R² is selected from the group consisting of: 2-hydroxypyridinyl, 1-methyl-2-oxo-1,2-dihydro-pyridinyl and 2-oxo-1-propyl-1,2-dihydro-pyridinyl.

A particular embodiment of the present invention are compounds according to formula (I) as described above, wherein R² is 2-hydroxypyridinyl.

A further embodiment of the present invention are compounds according to formula (I) as described above, wherein R² is 1-methyl-2-oxo-1,2-dihydro-pyridinyl or 2-oxo-1-propyl-1,2-dihydro-pyridinyl.

The present invention also relates to compounds according to formula (I) as described above, wherein n is zero.

Particular examples of compounds of formula (I) as described above are selected from the group consisting of:
8-(2-Fluoro-4-trifluoromethyl-phenyl)-2-(4-trifluoromethoxy-phenyl)-2,8-diaza-spiro[4.5]decan-1-one;
8-(2-Fluoro-5-trifluoromethyl-phenyl)-2-(4-trifluoromethoxy-phenyl)-2,8-diaza-spiro[4.5]decan-1-one;
8-(2-Fluoro-phenyl)-2-(4-trifluoromethoxy-phenyl)-2,8-diaza-spiro[4.5]decan-1-one;
8-(3-Trifluoromethoxy-phenyl)-2-(4-trifluoromethoxy-phenyl)-2,8-diaza-spiro[4.5]decan-1-one;
8-(2-Chloro-phenyl)-2-(4-trifluoromethoxy-phenyl)-2,8-diaza-spiro[4.5]decan-1-one;
8-(2,6-Difluoro-phenyl)-2-(4-trifluoromethoxy-phenyl)-2,8-diaza-spiro[4.5]decan-1-one;
8-(2-Methoxy-phenyl)-2-(4-trifluoromethoxy-phenyl)-2,8-diaza-spiro[4.5]decan-1-one;
8-(2-Methoxy-5-methyl-phenyl)-2-(4-trifluoromethoxy-phenyl)-2,8-diaza-spiro[4.5]decan-1-one;
8-(2-Methoxy-pyridin-3-yl)-2-(4-trifluoromethoxy-phenyl)-2,8-diaza-spiro[4.5]decan-1-one;
8-(2-fluoro-5-methylpyridin-3-yl)-2-(4-(trifluoromethoxy)phenyl)-2,8-diazaspiro[4.5]decan-1-one;
8-(1-methyl-2-oxo-1,2-dihydropyridin-3-yl)-2-(4-(trifluoromethoxy)phenyl)-2,8-diazaspiro[4.5]decan-1-one;
8-(2-Oxo-1-propyl-1,2-dihydro-pyridin-3-yl)-2-(4-trifluoromethoxy-phenyl)-2,8-diaza-spiro[4.5]decan-1-one;
8-(2-Hydroxy-phenyl)-2-(4-trifluoromethoxy-phenyl)-2,8-diaza-spiro[4.5]decan-1-one;
8-(2-Hydroxy-5-methyl-phenyl)-2-(4-trifluoromethoxy-phenyl)-2,8-diaza-spiro[4.5]decan-1-one;
8-(2-Hydroxy-pyridin-3-yl)-2-(4-trifluoromethoxy-phenyl)-2,8-diaza-spiro[4.5]decan-1-one;
8-(6-Benzyloxy-pyridin-2-yl)-2-(4-trifluoromethoxy-phenyl)-2,8-diaza-spiro[4.5]decan-1-one;
8-(6-Hydroxy-pyridin-2-yl)-2-(4-trifluoromethoxy-phenyl)-2,8-diaza-spiro[4.5]decan-1-one;
8-(1-Methyl-2-oxo-1,2-dihydro-pyridin-3-yl)-2-[4-((S)-2,2,2-trifluoro-1-methyl-ethoxy)-phenyl]-2,8-diaza-spiro[4.5]decan-1-one;
and pharmaceutically acceptable salts thereof.

Further particular examples of compounds of formula (I) as described above are selected from the group consisting of:
8-(2-Oxo-1-propyl-1,2-dihydro-pyridin-3-yl)-2-(4-trifluoromethoxy-phenyl)-2,8-diaza-spiro[4.5]decan-1-one;
8-(2-Hydroxy-phenyl)-2-(4-trifluoromethoxy-phenyl)-2,8-diaza-spiro[4.5]decan-1-one;
8-(1-Methyl-2-oxo-1,2-dihydro-pyridin-3-yl)-2-[4-((S)-2,2,2-trifluoro-1-methyl-ethoxy)-phenyl]-2,8-diaza-spiro[4.5]decan-1-one;
and pharmaceutically acceptable salts thereof.

Processes for the manufacture of compounds of formula (I) as described above are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

Compounds of formula (I) are readily accessible as outlined in Scheme 1 by a transition metal catalysed amination reaction, e.g a palladium catalysed amination reaction, known to the man skilled in the art or mentioned in. Angew. Chem. Int. Ed. 1998, 37, 2046-2067.

Scheme 1

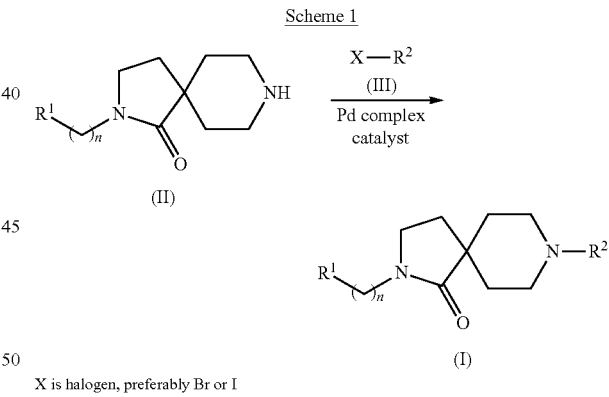

X is halogen, preferably Br or I

Thus, compounds of formula (I) can be prepared by reacting compounds of general formula (II) with a compound of general formula (III), wherein X is halogen, particularly iodo or bromo, in the presence of a palladium complex such as tris(dibenzylidene acetone)dipalladium-(0) and rac 2,2'-bis(diphenylphosphanyl)-1,1'-binaphthyl (rac-BINAP) as catalysts and Na$^t$OBu as base, in an appropriate solvent such as toluene at elevated temperature.

Alternatively compounds of formula (I) can be prepared by nucleophilic displacement reactions (Scheme 2). Thus suitable activated compounds of formula (II) are reacted with compounds of general formula (III) formula, wherein X is halogen, particularly chloro or fluoro, in the presence of a base such as NaH in DMF.

Scheme 2

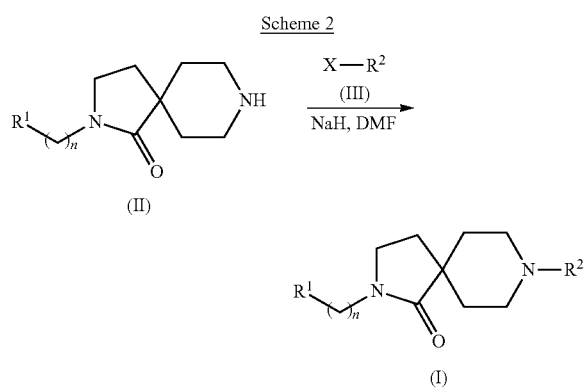

X is halogen, preferably Cl or F

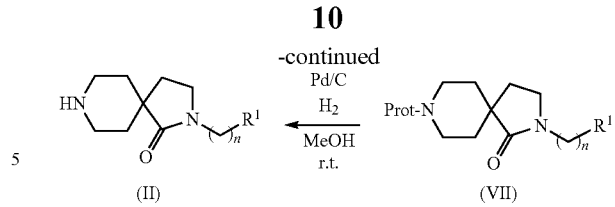

X is halogen, preferably Cl or Br
Alkyl is e.g. methyl or ethyl
Prot is Protecting group, e.g. Bn Also an embodiment of the present invention is a process to prepare a compound of formula (I) as defined above comprising the reaction of a compound of formula (II) in the presence of a compound of formula (III);

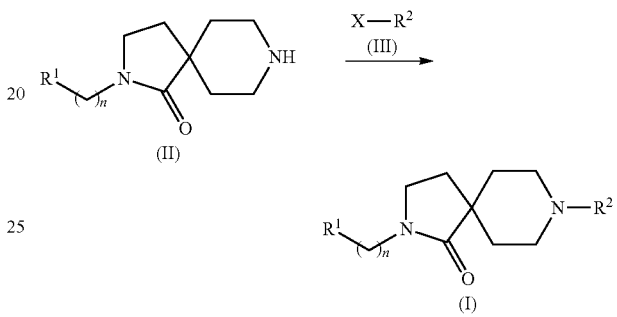

In particular in the presence of a base, particularly sodium hydride or tBuONa, in the presence or not of a palladium complex as catalyst, particularly tris(dibenzylidene acetone) dipalladium-(0) or rac 2,2'-bis(diphenylphosphanyl)-1,1'-binaphthyl (rac-BINAP), in a solvent, particularly toluene or DMF, at a temperature comprised between RT and reflux, wherein $R^1$, $R^2$ and n are as defined above and X is halogen, particularly iodine or bromine.

Particular intermediates are selected from the group consisting of:

8-Benzyl-2-(4-trifluoromethoxy-phenyl)-2,8-diaza-spiro[4.5]decan-1-one;

2-(4-Trifluoromethoxy-phenyl)-2,8-diaza-spiro[4.5]decan-1-one; and

2-[4-((S)-2,2,2-trifluoro-1-methylethoxy)-phenyl]-2,8-diaza-spiro[4.5]decan-1-one.

A further object of the present invention comprises a compound according to formula (I) as described above, when manufactured according to any one of the described processes.

Also an object of the present invention is a compound according to formula (I) as described above for use as therapeutically active substance.

Likewise an object of the present invention is a pharmaceutical composition comprising a compound according to formula (I) as described above and a therapeutically inert carrier.

Also an object of the present invention is the use of a compound according to formula (I) as described above for the treatment or prophylaxis of illnesses which are caused by disorders associated with e.g. the enzyme hormone-sensitive lipase.

The present invention also relates to the use of a compound according to formula (I) as described above for the treatment or prophylaxis of diabetes, metabolic syndrome, dyslipidemia, atherosclerosis or obesity.

Compounds of general formula (II) are readily accessible in a stepwise process as outlined in Scheme 3. For example suitable protected compound of formula general (IV) such as commercially available 1-benzyl-piperidine-4-carboxylic acid ethyl ester is alkylated by treatment with a suitable base such as lithium diisopropylamide in an appropriate solvent such as THF followed by the addition of 1-bromo-2-methoxyethane or 1-chloro-2-methoxyethane as the electrophile to give compound of general formula (V). Subsequent formation of compound of general formula (VII) can be achieved as by treatment of compounds of general formula (V) with an amine of general formula (VI) and dimethylaluminium chloride in a solvent such as toluene at reflux temperature. Alternatively, dioxane can be used as solvent and trimethylaluminium as the organometallic reagent. Subsequent deprotection gives compounds of general formula (II).

Scheme 3

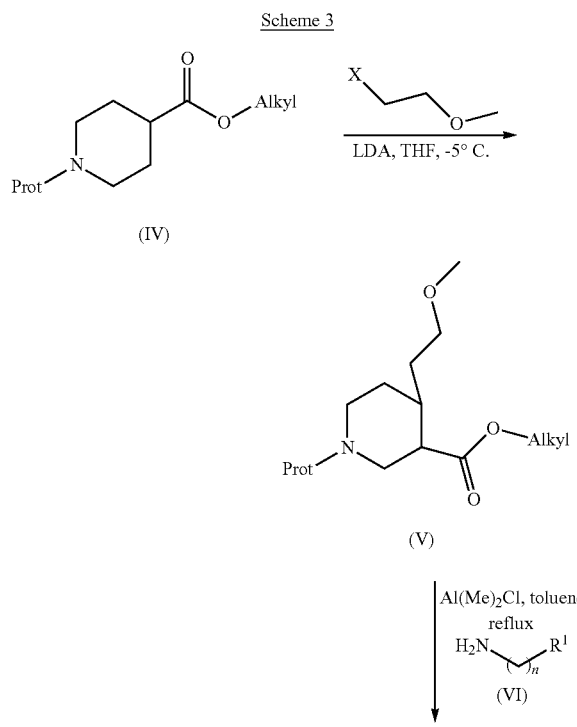

Also an embodiment of the present invention is the use of a compound according to formula (I) as described above for the treatment or prophylaxis of cardiovascular diseases, myocardial dysfunction, inflammation, nonalkoholic fatty liver disease or nonalkoholic steatohepatitis.

A particular embodiment of the present invention is the use of a compound according to formula (I) as described above for the treatment or prophylaxis of diabetes.

A further particular embodiment of the present invention is the use of a compound according to formula (I) as described above for the treatment or prophylaxis of diabetes Type II.

The present invention also relates to the use of a compound according to formula (I) as described above for the preparation of a medicament for the treatment or prophylaxis of diabetes, metabolic syndrome, dyslipidemia, atherosclerosis or obesity.

Also an embodiment of the present invention is the use of a compound according to formula (I) as described above for the preparation of a medicament for the treatment or prophylaxis of cardiovascular diseases, myocardial dysfunction, inflammation, nonalkoholic fatty liver disease or nonalkoholic steatohepatitis.

A particular embodiment of the present invention is the use of a compound according to formula (I) as described above for the preparation of medicaments for the treatment or prophylaxis of diabetes.

A further particular embodiment of the present invention is the use of a compound according to formula (I) as described above for the preparation of medicaments for the treatment or prophylaxis of diabetes Type II.

A particular embodiment of the present invention is a compound according to formula (I) as described above for the treatment or prophylaxis of diabetes, metabolic syndrome, dyslipidemia, atherosclerosis or obesity.

Also a particular embodiment of the present invention is a compound according to formula (I) as described above for the treatment or prophylaxis of cardiovascular diseases, myocardial dysfunction, inflammation, nonalkoholic fatty liver disease or nonalkoholic steatohepatitis.

A further particular embodiment of the present invention is a compound according to formula (I) as described above for the treatment or prophylaxis of diabetes.

Also a further particular embodiment of the present invention is a compound according to formula (I) as described above for the treatment or prophylaxis of diabetes Type II.

Also an object of the invention is a method for the treatment or prophylaxis of diabetes, metabolic syndrome, dyslipidemia, atherosclerosis or obesity, which method comprises administering an effective amount of a compound according to formula (I) as described above.

Also an embodiment of the present invention is a method for the treatment or prophylaxis of cardiovascular diseases, myocardial dysfunction, inflammation, nonalkoholic fatty liver disease or nonalkoholic steatohepatitis, which method comprises administering an effective amount of a compound according to formula (I) as described above.

A particular embodiment of the present invention is a method for the treatment or prophylaxis of diabetes, which method comprises administering an effective amount of a compound according to formula (I) as described above.

A further particular embodiment of the present invention is a method for the treatment or prophylaxis of diabetes Type II, which method comprises administering an effective amount of a compound according to formula (I) as described above.

Assay Procedures

Production of Human full length Hormone Sensitive Lipase-His$^6$:
1) Cloning: cDNA was prepared from commercial human brain polyA+ RNA and used as a template in overlapping PCR to generate a full length human HSL ORF with a 3'-His6 tag. This full length insert was cloned into the pFast-BAC vector and the DNA-sequence of several single clones was verified. DNA from a correct full length clone with the 3'His6 tag was used to transform the E. coli strain DH10BAC. Resulting bacmid DNA was used to generate a titered baculovirus stock for protein generation. The sequence of the encoded HSL conforms to Swissprot entry Q05469, with the additional C-terminal His6-tag.

2) Protein purification: Culture: 5.5 L, High 5 cells expressing human full length HSL-His$^6$, 48 hr., containing 25 µM E-64. Cell count: $1.78 \times 10^{10}$ cells/ml, 90% viable. Cells were thawed. On ice, cells were suspended in Base Buffer containing 10% glycerol, 25 mM Tris-Cl, 300 mM NaCl, 10 mM imidazole, 10 mM 2-mercaptoethanol, 2 µg pepstatin/ml, 2 µg leupeptin/ml, 2 µg antipain/ml, pH 8.0 at 4° C. in a final volume of 475 ml with $3.75 \times 10^7$ cells/ml. Sanitation was done at 3×30 sec., Lubrol PX was added to 0.2% final concentration followed by stirring for 15 min. at 4° C. and centrifugation at 25 k×g, 60 min., 4° C. Soluble proteins were mixed with 60 ml of pre-washed and equilibrated Ni-NTA Agarose (Qiagen 30210) followed by tumbling end-over-end, 45 min., 4° C., centrifugation 1000 rpm 5 min and letting resin settle 5 min. Supernatant was removed, the resin washed in the centrifuge vessel using 5 volumes of Base Buffer containing 0.2% Lubrol PX. Centrifugation was done again, then the supernatant discarded. The resin was poured onto a 0.8 µm membrane in a disposable filter unit (Nalge 450-0080), and washed with 5 volumes of Base Buffer containing 0.2% Lubrol PX. It was then washed with 30 volumes of Base Buffer containing 60 mM imidazole pH 7.5 at 4° C. The protein was eluated with 5 volumes of 25 mM Tris-Cl, 300 mM NaCl, 200 mM imidazole, 10 mM 2-mercaptoethanol, pH 7.5 at 4° C. by tumbling resin with buffer end-over-end, 30 min., 4° C. The resin was captured on a 0.2 µm membrane disposable filter unit (Millipore SCGP U02 RE) and the eluate collected in the reservoir. The eluate was concentrated using a 30 k MWCO centrifugal filter device (Sartorius Vivascience Vivacell 100, VC1022), to 20 ml. It was then dialyzed overnight at 4° C., two times against 2 L of 10% glycerol, 25 mM Tris-Cl, 300 mM NaCl, 0.2 mM EDTA, 0.2 mM DTT, pH 7.5 at 4° C. The protein was filtered using a 0.22 µm disposable filter unit (Millipore SCGP00525). The protein concentration was calculated from absorbance at 280 nm, using 280=0.67 cm-1 mg-1. Yield was 235 mg, total. The protein was stored at −80° C.

Human Hormone-Sensitive Lipase (HSL) Enzyme Inhibition Assay:

HSL enzyme activity was measured by a colorimetric assay using 2,3-dimercapto-1-propanol tributyrate (Aldrich, St. Louis, Mo.) as a substrate. Typically, 1.5 mM 2,3-dimercapto-1-propanol tributyrate (DMPT) in 100 mM MOPS, pH 7.2, 0.2 mg/ml fatty acid-free BSA was prepared by sonication at 4° C. to homogenous suspension. Test compounds (2 mM stock in DMSO) were diluted 3 fold in series in DMSO. Compound solutions were diluted 24 fold in 1.5 mM DMPT containing solution and 18 ul per well was added to 384-well microplates (Corning Costar). Twelve microliters per well of human HSL (15 ug/ml) was added and the reaction mixture was incubated at 37° C. for 20 minutes. Six microliters of 12 mM dithio-bis-(2-nitrobenzoic acid) (DTNB) in DMSO plus 1.2% SDS and 0.6% Triton X-100 were added and the mixture was incubated at room temperature for 15 minutes. Product production was monitored by reading absorbance at 405 nm on an Envision Reader (PerkinElmer Life and Analytical Sciences, Shelton, Conn.).

Cellular Assay:

The following assay was used to measure the effect of the compounds to inhibit lipolysis in intact cells (adipocytes). 3T3-L1 pre-adipocyte cells were plated into 96-well plates at a density of 20,000 cells/well in 200 ul growth media (DMEM/10% Calf Serum/1× antibiotic-antimycotic) until confluent. At 48 hours post-confluency, the medium was removed and the cells were differentiated into adipocytes with differentiation medium (DMEM/10% FBS/1× Antibiotic-Antimycotic PLUS: 1 uM IBMX (3-Isobutyl-1-methylxanthine) Inhibitor of phosphodiesterases, 1 uM Dexamethasone, 1 uM Rosiglitazone, 10 ug/ml Insulin). The cells were incubated in said medium for 3 days and then medium was changed to post-differentiation medium (DMEM/10% FBS PLUS: 10 ug/ml Insulin) and the cells were incubated for an additional 3 days. The medium was then changed to maintenance media (DMEM/10% FBS). The cells were fed every 3 days with maintenance media until use. The lipolysis assay may be performed on day 9-14 after the initiation of differentiation in 96 well plates.

The lipolysis assay was performed as follows. The adipocytes were washed 2× with 200 ul Krebs Ringer Bicarbonate Hepes buffer (KRBH)/3% BSA. Test compounds were at 10 mM in DMSO and were initially diluted to 5 mM in DMSO. They were then serially diluted 5-fold in DMSO (5 mM to 320 pM). Each compound was then diluted 200-fold into KRBH/3% BSA (0.5% DMSO final). The resulting solutions range from 25 uM to 1.6 pM final. One hundred fifty ul of the diluted compounds were added to each well (in triplicate) and the cells were preincubated 30 min at 37° C. Forskolin (50 uM final) was added to the wells and the cells were incubated 120 minutes at 37° C. One hundred ul was collected into a new 96-well plate for glycerol analysis. The amount of glycerol produced was determined using a glycerol determination kit (Sigma).

| Examples | HSL hum IC50 (uM) |
|---|---|
| 1 | 0.92 |
| 2 | 0.55 |
| 3 | 0.31 |
| 4 | 0.63 |
| 5 | 0.71 |
| 6 | 0.96 |
| 7 | 0.11 |
| 8 | 0.1 |
| 9 | 0.11 |
| 10 | 0.24 |
| 11 | 0.02 |
| 12 | 0.03 |
| 13 | 0.05 |
| 14 | 0.06 |
| 15 | 0.04 |
| 16 | 0.9 |
| 17 | 0.25 |
| 18 | 0.02 |

Compounds of formula (I) and their pharmaceutically acceptable salts or esters thereof as described above have $IC_{50}$ values between 0.0001 uM and 1000 uM, particular compounds have $IC_{50}$ values between 0.001 uM and 500 uM, further particular compounds have $IC_{50}$ values between 0.001 uM and 5 uM. These results have been obtained by using the foregoing HSL enzyme inhibition assay (uM means microMolar).

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention, the compounds of formula (I) and their pharmaceutically acceptable salts can be used for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

Example 1

8-(2-Fluoro-4-trifluoromethyl-phenyl)-2-(4-trifluoromethoxy-phenyl)-2,8-diaza-spiro[4.5]decan-1-one

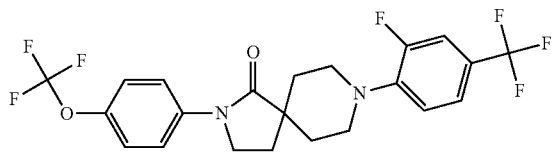 [SMILES: O=C1N(c2ccc(OC(F)(F)F)cc2)CCC12CCN(c1ccc(C(F)(F)F)cc1F)CC2]

Step A: 1-Benzyl-4-(2-methoxy-ethyl)-piperidine-4-carboxylic acid ethyl ester

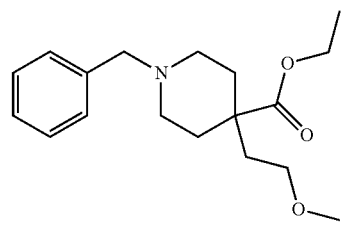 [SMILES: CCOC(=O)C1(CCOC)CCN(Cc2ccccc2)CC1]

To a solution of diisopropylamine (5.68 mL, 0.040 mol) in 100 ml THF at −78° C. was added nBuli (1.6M solution in hexane, 25.9 mL, 0.041 mol) drop-wise. The reaction mixture was warmed to −5° C. and stirring was continued for 30 mins. A solution of 1-benzylpiperidine-4-carboxylic acid ethyl ester (5.00 g, 0.020 mol) in THF (20 mL) was added drop wise and stirring was continued for a further 3 hr followed by the addition of a solution of 1-bromo-2-methoxy-ethane (3.82 g, 0.040 mol) in THF (20 mL) at −5° C. The reaction mixture was then allowed to warm to room temperature and stirring was continued overnight. The reaction mixture was quenched with water and concentrated in vacuo to give a brown residue which was diluted with ethyl acetate and extracted 1NHCl. The aqueous layers were then combined, made basic (with 1N NaOH) and extracted with ethyl acetate. The organic layers were combined, washed with brine, dried ($Na_2SO_4$), filtered and concentrated in vacuo to give a crude residue which was purified by flash column chromatography (1:1 AcOEt/heptane) to give 1-benzyl-4-(2-methoxyethyl)-piperidine-4-carboxylic acid ethyl ester (5.2 g, 84%) as a brown oil. MS (ESI): 306.3 (MH+).

Step B: 8-Benzyl-2-(4-trifluoromethoxy-phenyl)-2,8-diaza-spiro[4.5]decan-1-one

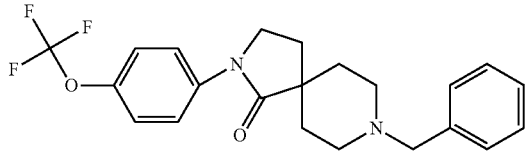 [SMILES: O=C1N(c2ccc(OC(F)(F)F)cc2)CCC12CCN(Cc1ccccc1)CC2]

To a solution of 1-benzyl-4-(2-methoxyethyl)-piperidine-4-carboxylic acid ethyl ester (5.2 g, 0.017 mol) and 4-(trifluormethoxy)aniline (4.57 ml, 0.034 mol) in toluene (200 ml) under an argon atmosphere at room temperature, was added dimethylaluminium chloride (0.9M solution in heptane, 37 ml, 0.034 mol) and the mixture was refluxed for 4 hours. The reaction mixture was cooled to room temperature and quenched was sat. $Na_2SO_{4(aq)}$ solution and the mixture was filtered through Celite® and evaporated under reduced pressure. The crude residue was purified by flash column chromatography (1:3 AcOEt/heptane) to give 8-benzyl-2-(4-trifluoromethoxy-phenyl)-2,8-diaza-spiro[4.5]decan-1-one as a white solid. MS (ESI): 405.4 (MH+).

Step C 2-(4-Trifluoromethoxy-phenyl)-2,8-diaza-spiro[4.5]decan-1-one

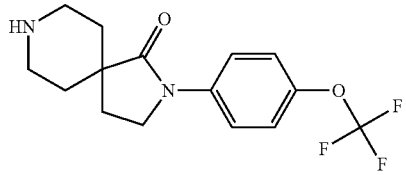 [SMILES: O=C1N(c2ccc(OC(F)(F)F)cc2)CCC12CCNCC2]

A mixture of 8-benzyl-2-(4-trifluoromethoxy-phenyl)-2,8-diaza-spiro[4.5]decan-1-one (3.14 g, 0.007 mol), acetic acid (5 ml) and Pearlman's catalyst (0.43 mg) in MeOH (40 ml) was stirred at room temperature under an atmospheric pressure of $H_2$ for 3 h. The catalyst was removed by filtration and the filtrate was evaporated to give a crude residue which was triturated with diethyl ether (50 ml) to give 2-(4-trifluoromethoxy-phenyl)-2,8-diaza-spiro[4.5]decan-1-one; acetic acid salt as a white solid (1.43 g, 49%). MS (ESI): 315.1 (MH+).

The acetic acid salt could be liberated in the following manner: The resulting residue was dissolved in water and the solution was made basic with 1N NaOH and extracted with ethyl acetate. The combined organic extracts were dried ($Na_2SO_4$), filtered and evaporated under reduced pressure to yield 2-(4-trifluoromethoxy-phenyl)-2,8-diaza-spiro[4.5]decan-1-one as an off white solid. MS (ESI): 315.1 (MH+).

Step D 8-(2-Fluoro-4-trifluoromethyl-phenyl)-2-(4-trifluoromethoxy-phenyl)-2,8-diaza-spiro[4.5]decan-1-one

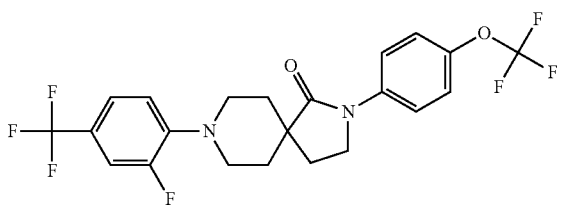 [SMILES: O=C1N(c2ccc(OC(F)(F)F)cc2)CCC12CCN(c1ccc(C(F)(F)F)cc1F)CC2]

A sealed tube was charged with 4-bromo-3-fluorobenzotrifluoride (40 mg, 0.16 mmol), 2-(4-trifluoromethoxy-phenyl)-2,8-diaza-spiro[4.5]decan-1-one (50 mg, 0.16 mmol), sodium tert-butoxide (17 mg, 0.18 mmol), tris(dibenzylidene acetone)dipalladium-(0) (15 mg, 0.02 mmol), BINAP (5 mg, 0.01 mmol) and toluene (2) under argon. The sealed tube was closed and immersed in an oil bath and heated to 80° C. for 15 h. The reaction mixture was allowed to cool to room temperature, diluted in ethyl acetate, filtered, and concentrated in vacuo to give a crude residue which was purified by flash column chromatography to yield the title compound as a light yellow solid (50 mg, 66%). MS (ESI): 477.1 (MH+)

Example 2

8-(2-Fluoro-5-trifluoromethyl-phenyl)-2-(4-trifluoromethoxy-phenyl)-2,8-diaza-spiro[4.5]decan-1-one

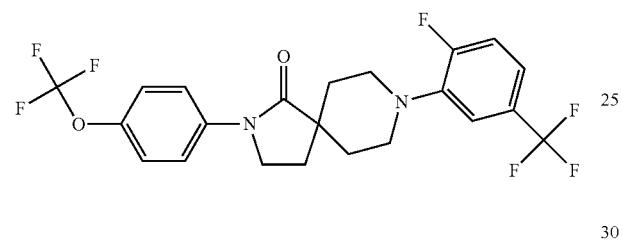

The title compound was prepared in analogy to example 1 step D from a mixture of 2-(4-trifluoromethoxy-phenyl)-2,8-diaza-spiro[4.5]decan-1-one (described in example 1 step C) and 2-bromo-1-fluoro-4-trifluoromethyl-benzene. Light yellow solid. MS (ESI): 477.1 (MH$^+$)

Example 3

8-(2-Fluoro-phenyl)-2-(4-trifluoromethoxy-phenyl)-2,8-diaza-spiro[4.5]decan-1-one

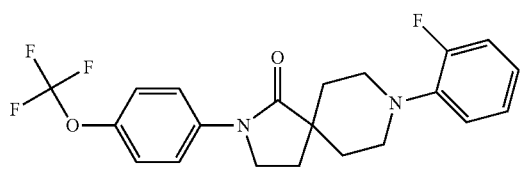 [SMILES: O=C1N(c2ccc(OC(F)(F)F)cc2)CCC12CCN(c1ccccc1F)CC2]

The title compound was prepared in analogy to example 1 step D from a mixture of 2-(4-trifluoromethoxy-phenyl)-2,8-diaza-spiro[4.5]decan-1-one (described in example 1 step C) and 2-bromofluoro benzene. White solid. MS (ESI): 409.2 (MH$^+$)

Example 4

8-(3-Trifluoromethoxy-phenyl)-2-(4-trifluoromethoxy-phenyl)-2,8-diaza-spiro[4.5]decan-1-one

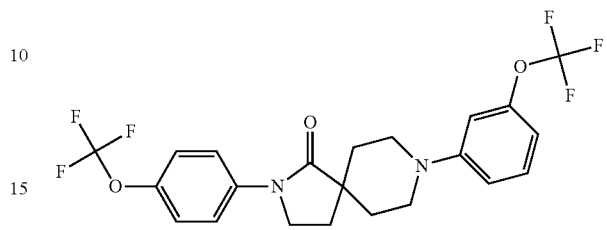

The title compound was prepared in analogy to example 1 step D from a mixture of 2-(4-trifluoromethoxy-phenyl)-2,8-diaza-spiro[4.5]decan-1-one (described in example 1 step C) and 1-bromo-3-trifluoromethoxy-benzene. Light yellow solid. MS (ESI): 475.1 (MH$^+$)

Example 5

8-(2-Chloro-phenyl)-2-(4-trifluoromethoxy-phenyl)-2,8-diaza-spiro[4.5]decan-1-one

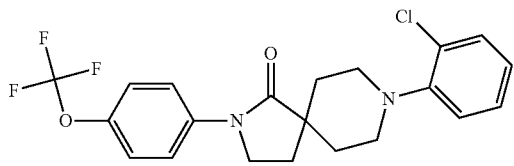

The title compound was prepared in analogy to example 1 step D from a mixture of 2-(4-trifluoromethoxy-phenyl)-2,8-diaza-spiro[4.5]decan-1-one (described in example 1 step C) and 2-bromoclorobenzene. Light yellow solid. MS (ESI): 425.1 (MH$^+$)

Example 6

8-(2,6-Difluoro-phenyl)-2-(4-trifluoromethoxy-phenyl)-2,8-diaza-spiro[4.5]decan-1-one

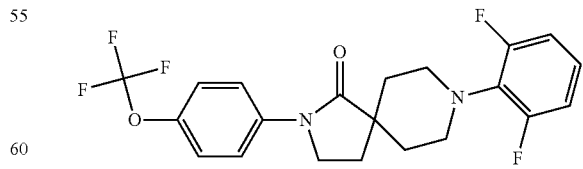

The title compound was prepared in analogy to example 1 step D from a mixture of 2-(4-trifluoromethoxy-phenyl)-2,8-diaza-spiro[4.5]decan-1-one (described in example 1 step C) and 1-bromo-2,6-difluorobenzene. White solid. MS (ESI): 427.1 (MH$^+$)

Example 7

8-(2-Methoxy-phenyl)-2-(4-trifluoromethoxy-phenyl)-2,8-diaza-spiro[4.5]decan-1-one

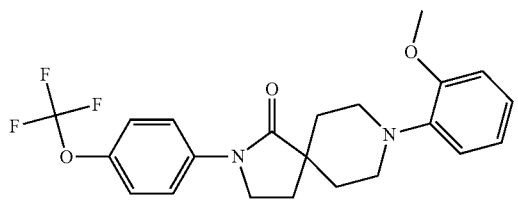 [SMILES: COc1ccccc1N1CCC2(CC1)CCN(c1ccc(OC(F)(F)F)cc1)C2=O]

The title compound was prepared in analogy to example 1 step D from a mixture of 2-(4-trifluoromethoxy-phenyl)-2,8-diaza-spiro[4.5]decan-1-one (described in example 1 step C) and 2-bromoanisole. Light yellow solid. MS (ESI): 421.0 (MH$^+$)

Example 8

8-(2-Methoxy-5-methyl-phenyl)-2-(4-trifluoromethoxy-phenyl)-2,8-diaza-spiro[4.5]decan-1-one

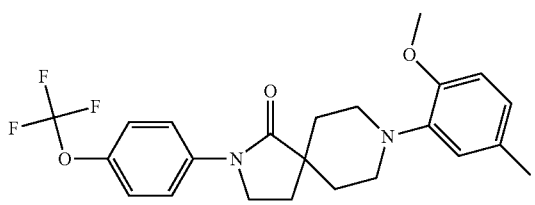 [SMILES: COc1ccc(C)cc1N1CCC2(CC1)CCN(c1ccc(OC(F)(F)F)cc1)C2=O]

The title compound was prepared in analogy to example 1 step D from a mixture of 2-(4-trifluoromethoxy-phenyl)-2,8-diaza-spiro[4.5]decan-1-one (described in example 1 step C) and 2-bromo-4-methylanisole. Light yellow solid. MS (ESI): 435.3 (MH$^+$)

Example 9

8-(2-Methoxy-pyridin-3-yl)-2-(4-trifluoromethoxy-phenyl)-2,8-diaza-spiro[4.5]decan-1-one

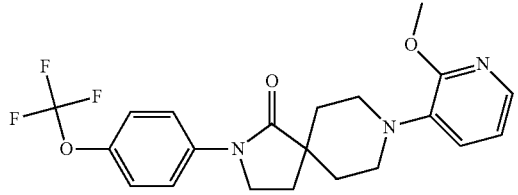 [SMILES: COc1ncccc1N1CCC2(CC1)CCN(c1ccc(OC(F)(F)F)cc1)C2=O]

The title compound was prepared in analogy to example 1 step D from a mixture of 2-(4-trifluoromethoxy-phenyl)-2,8-diaza-spiro[4.5]decan-1-one (described in example 1 step C) and 3-bromo-2-methoxypyridine. Light yellow solid. MS (ESI): 422.1 (MH$^+$)

Example 10

8-(2-fluoro-5-methylpyridin-3-yl)-2-(4-(trifluoromethoxy)phenyl)-2,8-diazaspiro[4.5]decan-1-one

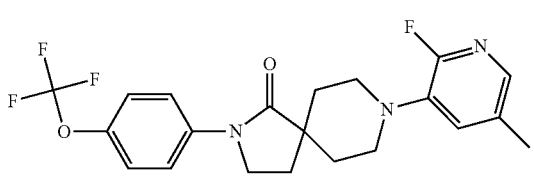

The title compound was prepared in analogy to example 1 step D from a mixture of 2-(4-trifluoromethoxy-phenyl)-2,8-diaza-spiro[4.5]decan-1-one (described in example 1 step C) and 3-bromo-2-fluoro-5-methylpyridine. Light yellow solid. MS (ESI): 424.1 (MH$^+$)

Example 11

8-(1-methyl-2-oxo-1,2-dihydropyridin-3-yl)-2-(4-(trifluoromethoxy)phenyl)-2,8-diazaspiro[4.5]decan-1-one

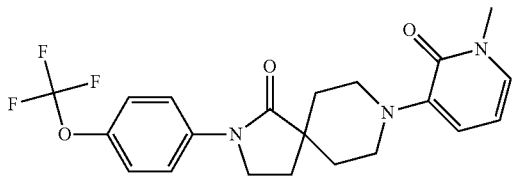 [SMILES: Cn1cccc(N2CCC3(CC2)CCN(c2ccc(OC(F)(F)F)cc2)C3=O)c1=O]

The title compound was prepared in analogy to example 1 step D from a mixture of 2-(4-trifluoromethoxy-phenyl)-2,8-diaza-spiro[4.5]decan-1-one (described in example 1 step C) and 3-bromo-1-methyl-1H-pyridin-2-one. Light yellow solid. MS (ESI): 422.1 (MH$^+$)

Example 12

8-(2-Oxo-1-propyl-1,2-dihydro-pyridin-3-yl)-2-(4-trifluoromethoxy-phenyl)-2,8-diaza-spiro[4.5]decan-1-one

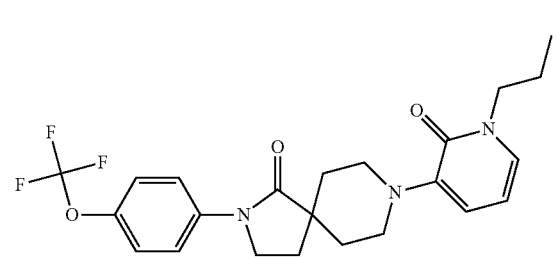 [SMILES: CCCn1cccc(N2CCC3(CC2)CCN(c2ccc(OC(F)(F)F)cc2)C3=O)c1=O]

The title compound was prepared in analogy to example 1 step D from a mixture of 2-(4-trifluoromethoxy-phenyl)-2,8- diaza-spiro[4.5]decan-1-one (described in example 1 step C) and 3-bromo-1-propyl-1H-pyridin-2-one. Off-white solid. MS (ESI): 450.2 (MH⁺)

Example 13

8-(2-Hydroxy-phenyl)-2-(4-trifluoromethoxy-phenyl)-2,8-diaza-spiro[4.5]decan-1-one

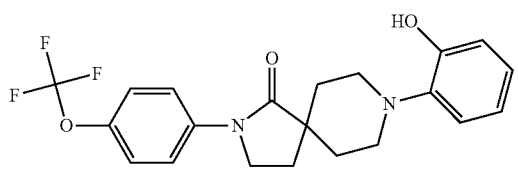 [SMILES: O=C1N(c2ccc(OC(F)(F)F)cc2)CCC12CCN(c1ccccc1O)CC2]

To a solution of 8-(2-methoxy-phenyl)-2-(4-trifluoromethoxy-phenyl)-2,8-diaza-spiro[4.5]decan-1-one (described in example 7, 16 mg, 0.04 mmol) in DCM (1 mL) at −78° C. was added borontribromide (1M, 110 uL, 0.12 mmol) drop wise. The reaction mixture was warmed to r.t. and stirring was continued overnight. The reaction mixture was quenched with sat. NaHCO₃ and extracted with DCM. The combined organic extracts were washed with brine, dried (Na₂SO₄), filtered and evaporated under reduced pressure to yield the title compound a white solid (9 mg, 61%). MS (ESI): 407.4 (MH+).

Example 14

8-(2-Hydroxy-5-methyl-phenyl)-2-(4-trifluoromethoxy-phenyl)-2,8-diaza-spiro[4.5]decan-1-one

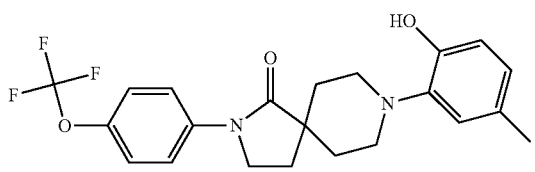 [SMILES: Cc1ccc(O)c(N2CCC3(CC2)CCN(c2ccc(OC(F)(F)F)cc2)C3=O)c1]

The title compound was prepared in analogy to example 13 from a mixture of 8-(2-methoxy-5-methyl-phenyl)-2-(4-trifluoromethoxy-phenyl)-2,8-diaza-spiro[4.5]decan-1-one (described in example 8) and boron tribromide. Light yellow solid. MS (ESI): 421.1 (MH⁺)

Example 15

8-(2-Hydroxy-pyridin-3-yl)-2-(4-trifluoromethoxy-phenyl)-2,8-diaza-spiro[4.5]decan-1-one

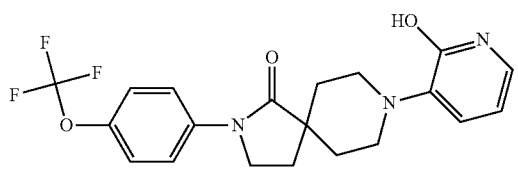 [SMILES: O=C1N(c2ccc(OC(F)(F)F)cc2)CCC12CCN(c1cccnc1O)CC2]

To a solution of 8-(2-methoxy-pyridin-3-yl)-2-(4-trifluoromethoxy-phenyl)-2,8-diaza-spiro[4.5]decan-1-one (described in example 9, 40 mg, 0.095 mmol) in acetonitrile (2 mL) at 0° C. was added NaI (28.5 mg, 0.19 mmol). TMSCl (24 uL, 0.19 mmol) was added, and the mixture was stirred and allowed to warm to rt over overnight. 1N Hydrochloric acid (1 mL), 38% aqueous sodium bisulfite solution (0.5 mL), brine and EtOAc (10 mL) were added, and the mixture was stirred for 30 min. The phases were separated, and the aqueous phase was extracted with additional EtOAc. The combined organic phases were washed with sat. NaHCO3, brine, dried (Na₂SO₄), filtered and evaporated under reduced pressure to yield the title compound as a light green solid (25 mg, 65%). MS (ESI): 408.3 (MH+).

Example 16

8-(6-Benzyloxy-pyridin-2-yl)-2-(4-trifluoromethoxy-phenyl)-2,8-diaza-spiro[4.5]decan-1-one

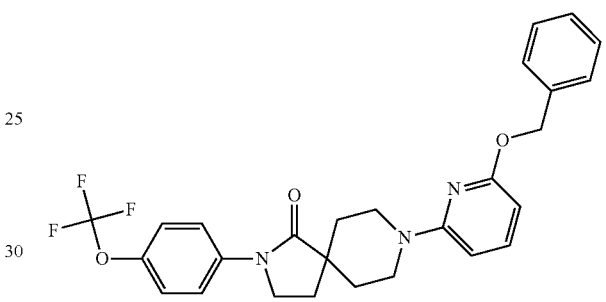

To a suspension of NaH (9 mg, 0.24 mmol) in DMF (1 mL) at 0° C. was added a solution of 2-(4-trifluoromethoxy-phenyl)-2,8-diaza-spiro[4.5]decan-1-one (described in example 1 step C, 50 mg, 0.16 mmol) and stirring was continued for 30 mins. A solution of 2-benzyloxy-6-fluoro-pyridine (39 mg, 0.19 mmol) in DMF (0.5 mL) was added and the mixture was stirred at room temperature for 2 h. The reaction mixture was diluted with ethyl acetate and washed with brine, 1N HCl and again with brine. The organic phase was dried (Na₂SO₄), filtered and evaporated under reduced pressure to yield the title compound as a light yellow solid (58 mg, 73%). MS (ESI): 498.2 (MH+).

Example 17

8-(6-Hydroxy-pyridin-2-yl)-2-(4-trifluoromethoxy-phenyl)-2,8-diaza-spiro[4.5]decan-1-one

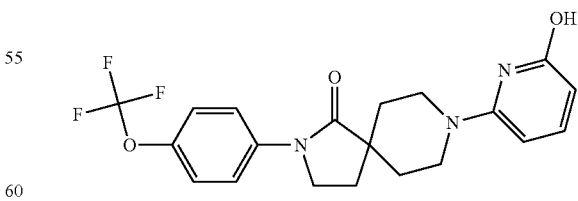

To a solution of 8-(6-benzyloxy-pyridin-2-yl)-2-(4-trifluoromethoxy-phenyl)-2,8-diaza-spiro[4.5]decan-1-one (58 mg, 0.12 mmol) in methanol (2 mL) was added palladium (0) (4 mg). The reaction mixture was stirred at room temperature under an atmospheric pressure of H₂ for 4 h and subsequently filtered. The filtrate was concentrated in vacuo and the crude residue was purified by flash column chromatography to yield the title compound (11 mg, 23%) as a white solid. MS (ESI): 408.3 (MH+)

Example 18

8-(1-Methyl-2-oxo-1,2-dihydro-pyridin-3-yl)-2-[4-((S)-2,2,2-trifluoro-1-methyl-ethoxy)-phenyl]-2,8-diaza-spiro[4.5]decan-1-one

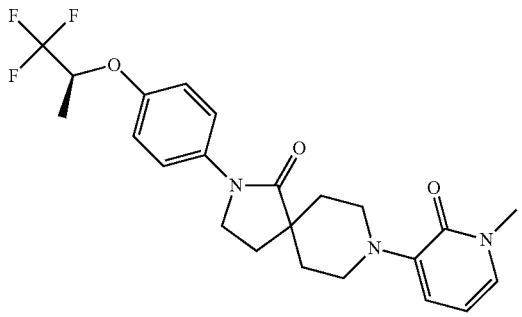 [SMILES: C[C@H](Oc1ccc(N2CCC3(CCN(c4cccn(C)c4=O)CC3)C2=O)cc1)C(F)(F)F]

The title compound was prepared in analogy to example 1 step D from a mixture of 2-[4-((S)-2,2,2-trifluoro-1-methyl-ethoxy)-phenyl]-2,8-diaza-spiro[4.5]decan-1-one (prepared in analogy to example 1 step B-C from 1-benzyl-4-(2-methoxyethyl)-piperidine-4-carboxylic acid ethyl ester and 4-((S)-2,2,2-trifluoro-1-methyl-ethoxy)-phenylamine) and 3-bromo-1-methyl-1H-pyridin-2-one. Light green solid. MS (ESI): 450.1 (MH+)

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound selected from the group consisting of:
   8-(2-Fluoro-4-trifluoromethyl-phenyl)-2-(4-trifluoromethoxy-phenyl)-2,8-diaza-spiro[4.5]decan-1-one;
   8-(2-Fluoro-5-trifluoromethyl-phenyl)-2-(4-trifluoromethoxy-phenyl)-2,8-diaza-spiro[4.5]decan-1-one;
   8-(2-Fluoro-phenyl)-2-(4-trifluoromethoxy-phenyl)-2,8-diaza-spiro[4.5]decan-1-one;
   8-(2-Chloro-phenyl)-2-(4-trifluoromethoxy-phenyl)-2,8-diaza-spiro[4.5]decan-1-one;
   8-(2,6-Difluoro-phenyl)-2-(4-trifluoromethoxy-phenyl)-2,8-diaza-spiro[4.5]decan-1-one;
   8-(2-Methoxy-pyridin-3-yl)-2-(4-trifluoromethoxy-phenyl)-2,8-diaza-spiro[4.5]decan-1-one;
   8-(2-fluoro-5-methylpyridin-3-yl)-2-(4-(trifluoromethoxy)phenyl)-2,8-diazaspiro[4.5]decan-1-one;
   8-(1-methyl-2-oxo-1,2-dihydropyridin-3-yl)-2-(4-(trifluoromethoxy)phenyl)-2,8-diazaspiro[4.5]decan-1-one;
   8-(2-Oxo-1-propyl-1,2-dihydro-pyridin-3-yl)-2-(4-trifluoromethoxy-phenyl)-2,8-diazaspiro[4.5]decan-1-one;
   8-(2-Hydroxy-phenyl)-2-(4-trifluoromethoxy-phenyl)-2,8-diaza-spiro[4.5]decan-1-one;
   8-(2-Hydroxy-5-methyl-phenyl)-2-(4-trifluoromethoxy-phenyl)-2,8-diaza-spiro[4.5]decan-1-one;
   8-(2-Hydroxy-pyridin-3-yl)-2-(4-trifluoromethoxy-phenyl)-2,8-diaza-spiro[4.5]decan-1-one;
   8-(6-Benzyloxy-pyridin-2-yl)-2-(4-trifluoromethoxy-phenyl)-2,8-diaza-spiro[4.5]decan-1-one;
   8-(6-Hydroxy-pyridin-2-yl)-2-(4-trifluoromethoxy-phenyl)-2,8-diaza-spiro[4.5]decan-1-one;
   8-(1-Methyl-2-oxo-1,2-dihydro-pyridin-3-yl)-2-[4-((S)-2,2,2-trifluoro-1-methyl-ethoxy)-phenyl]-2,8-diaza-spiro[4.5]decan-1-one;
   and pharmaceutically acceptable salts thereof.

2. A compound according to claim 1, selected from the group consisting of:
   8-(2-Oxo-1-propyl-1,2-dihydro-pyridin-3-yl)-2-(4-trifluoromethoxy-phenyl)-2,8-diazaspiro[4.5]decan-1-one;
   8-(2-Hydroxy-phenyl)-2-(4-trifluoromethoxy-phenyl)-2,8-diaza-spiro[4.5]decan-1-one; and
   8-(1-Methyl-2-oxo-1,2-dihydro-pyridin-3-yl)-2-[4-((S)-2,2,2-trifluoro-1-methyl-ethoxy)-phenyl]-2,8-diaza-spiro[4.5]decan-1-one;
   and pharmaceutically acceptable salts thereof.

3. A pharmaceutical composition comprising a compound according to claim 1 and a therapeutically inert carrier.

* * * * *

UNITED STATES PATENT AND TRADEMARK OFFICE
CERTIFICATE OF CORRECTION

| | | |
|---|---|---|
| PATENT NO. | : 8,552,024 B2 | Page 1 of 1 |
| APPLICATION NO. | : 13/204743 | |
| DATED | : October 8, 2013 | |
| INVENTOR(S) | : Jean Ackermann et al. | |

It is certified that error appears in the above-identified patent and that said Letters Patent is hereby corrected as shown below:

Title Page, Item (75) Inventors: should read as follows:

Jean Ackermann, Riehen, (CH);
Aurelia Conte, Basel, (CH);
Daniel Hunziker, Moehlin, (CH);
Werner Neidhart, Hagenthal-le-Bas, (FR);
Matthias Nettekoven, Grenzach-Wyhlen, (DE);
Tanja Schulz-Gasch, Ziefen, (CH);
Stanley Wertheimer, Croton, (US)

Signed and Sealed this
Tenth Day of December, 2013

Margaret A. Focarino
*Commissioner for Patents of the United States Patent and Trademark Office*